United States Patent [19]

Ryo

[11] Patent Number: 4,715,359

[45] Date of Patent: Dec. 29, 1987

[54] SAFETY BOTTLE AND CAP FOR THE ADMINISTRATION OF LIQUID RADIOACTIVE IODINE

[76] Inventor: U. Yun Ryo, 2716 Martinique La., Lexington, Ky. 40509

[21] Appl. No.: 845,259

[22] Filed: Mar. 28, 1986

[51] Int. Cl.⁴ ............ A61N 5/12

[52] U.S. Cl. ............ 128/1.1; 215/229; 215/309

[58] Field of Search ............ 128/1.1, 1 R; 215/309, 215/1 A, 229

[56] References Cited

U.S. PATENT DOCUMENTS

| | | | |
|---|---|---|---|
| 1,127,897 | 2/1915 | Kellogg | 128/1.1 |
| 2,264,099 | 11/1941 | Shaw | 215/309 X |
| 2,684,674 | 7/1959 | Archer | 215/309 X |
| 3,845,387 | 11/1974 | Slagle | 215/309 |
| 4,080,989 | 3/1978 | Chapelsky et al. | 215/309 X |
| 4,244,477 | 1/1981 | Seel | 215/229 |

*Primary Examiner*—Stephen C. Pellegrino
*Attorney, Agent, or Firm*—Milton S. Gerstein; Marvin Benn

[57] ABSTRACT

A safety cap for tightly closing a container having liquid radioactive iodine solution in it. The cap is provided with a pair of holes through which extend a pair of straws, each of the straws having an inner end in communication with the interior of the container. Each straw also has an outer end, one of which is insertable into the patient's mouth for drinking the liquid radioactive iodine solution in the container, and the other of which is insertable into a glass of water so that, after the patient has drunk most of the liquid radioactive iodine solution in the container, the residue of the solution in the bottle may be flushed out by forming a partial vacuum in the interior of the bottle, thereby causing the water in the glass to be drawn into the interior of the container to be mixed with the residue of the solution and, thereafter, to be drawn into the mouth and drunk by the patient. The dispenser, thus formed, prevents any accidental leakage of radioactivity from the liquid radioactive iodine solution to the ambient air and, therefore, to any person, such as a doctor or nurse, administering the dosage of liquid radioactive iodine solution. The safety cap also prevents accidental spilling of the liquid radioactive iodine solution during administration of the liquid to the patient, since access to the liquid in the container is provided by the straws, with the safety cap not removed from the bottle.

7 Claims, 4 Drawing Figures

FIG. 1
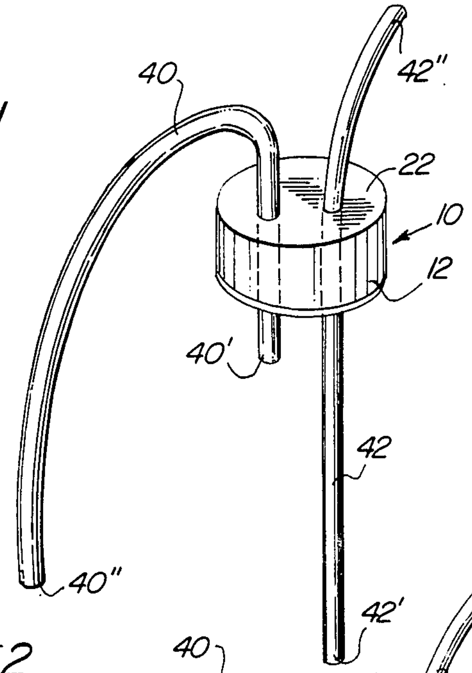
FIG. 2
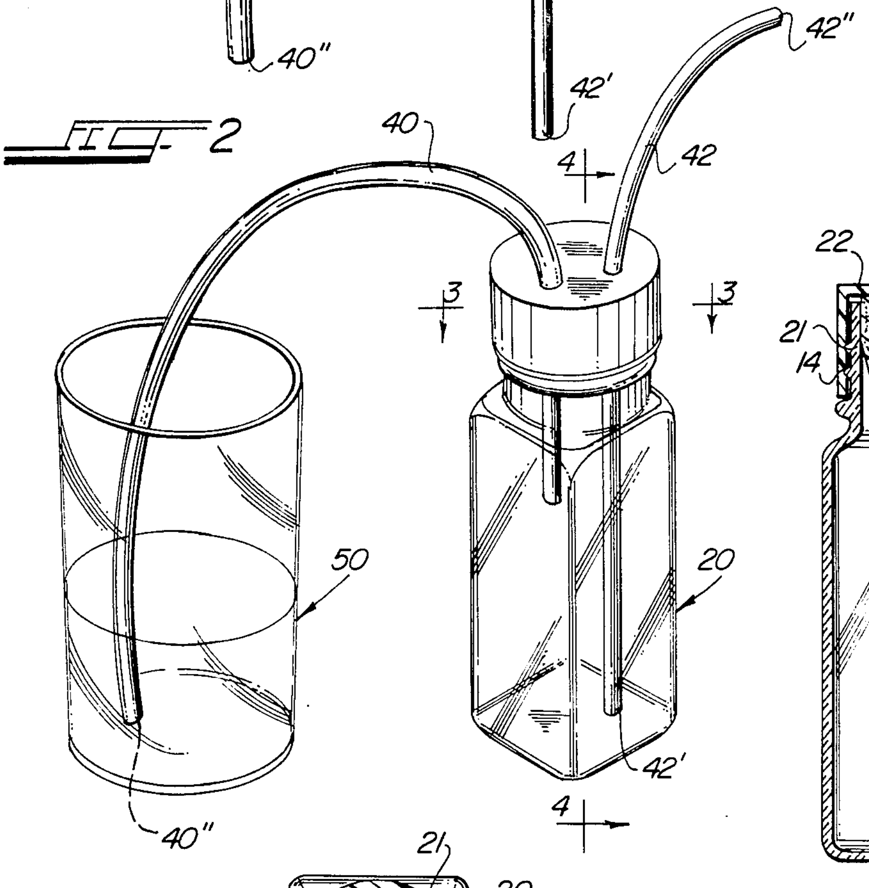
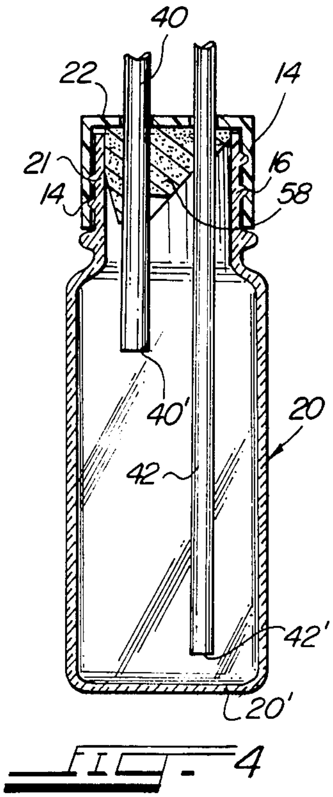
FIG. 4
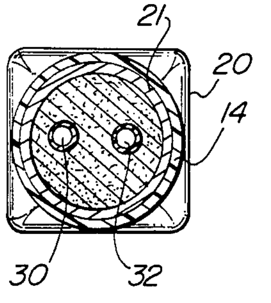
FIG. 3

SAFETY BOTTLE AND CAP FOR THE ADMINISTRATION OF LIQUID RADIOACTIVE IODINE

SUMMARY OF THE INVENTION

The present invention is directed to a cap or closure member for combination with a conventional bottle containing therein radioactive iodine. A well-known method of treatment for cancer of the thyroid gland is for the patient to imbibe liquid radioactive iodine, as a form of sodium iodide. Radioactive iodine (I-131) has proven successful in the treatment of this type of cancer, and the usual method by which such treatment is carried out is to have a patient drink the liquid solution of radioactive iodine from a straw inserted in a bottle containing the solution after removal of the cap of the bottle. Since this solution of liquid radioactive iodine is radioactive, it poses a health hazard to those who administer the liquid radioactive iodine over a period of time. That is to say each time a doctor, nurse or medical technician administers this liquid radioactive iodine by removing the cap of the bottle, he or she is exposed to radioactivity. Although the doctor, nurse or medical technicial will generally use gloves during such administration, it may happen that the solution will splash or spill. Further, it is inevitable that some of the radioactivity will leak to the ambient air by diffusion, as it is exposed to the air, thus exposing the medical personnel to such radioactivity. Over a substantial period of time, there is a potential health hazard posed to the medical personnel due to this radioactivity. At present, there is no safe means for administering this liquid radioactive iodine solution to a patient other than being extremely careful that the liquid does not spill or splash.

The general method of treating a patient with this liquid radioactive iodine solution is to have the patient drink the entire contents of the bottle containing the liquid solution via a straw, fill the bottle with water so as to combine any remaining solution with the water, and have the patient drink the water so that none of the liquid radioactive iodine solution is wasted. The steps of filling the bottle with water and subsequently drinking this water mixture is carried out several times. Thus, during the drinking of the pure liquid radioactive iodine solution in the bottle, and during several refillings of the bottle for subsequent drinking of the water mixture by the patient, the contents of the bottle are exposed to the ambient air for a substantial period of time, a time during which the medical personnel administering the liquid radioactive iodine solution may become contaminated. Further hazards are posed to the doctor or nurse administering the liquid radioactive iodine solution by their contact with the bottle, straw and cap of the bottle.

Another method currently available for the oral administration of radioactive iodine is the use of a sealed vial containing the radioactive iodine. A straw is attached to a long needle and the needle is used to puncture and penetrate the vial cap. This method requires two additional steps: (1) Another needle has to be used to allow in-flow of air into the vial as the content (I-131) is sucked-up by the patient through a straw; and (2) the second step needed is injection of drinking water into the vial, two to three times, in order to flush-out the entire dose of radioactive iodine. These steps force medical personnel to take the risk of contact to, and exposure to, the radioactive iodine. Also, the additional steps cause a higher risk of spillage of the radioactive iodine on a table top and on the floor. Spillage of radioactive iodine on the floor of the patient's room may cause hours of hard work for radiation officers, or may dictate closure of that patient's hospital room for a few weeks.

SUMMARY OF THE INVENTION

It is, therefore, the primary objective of the present invention to provide a safety cap for the administration of liquid radioactive iodine solution in pure form, and the mixture of the liquid radioactive iodine solution when mixed with water during the subsequent fillings of the liquid radioactive iodine container, so that the medical personnel administering the liquid radioactive iodine solution are not exposed to any potentially-hazardous radioactivity and prevent possible radioactivity spillage.

It is still another objective of the present invention to provide a safety cap that may be used to replace a standard cap provided on the container containing the liquid radioactive iodine solution, such that it may replace the container cap in an easy and simple manner, and in a room distinct from that in which the patient resides, so that replacement may be carried out by technicians suitably protected from potentially-hazardous radioactivity.

It is yet another object of the present invention to provide such a safety cap or closure member for a conventional liquid radioactive iodine solution container such that the usual method of administering the radioactive iodine solution may be carried out in a substantially normal manner as that previously used, including the subsequent refillings of the container with water and the subsequent drinking thereof by the patient.

It is yet another objective of the present invention to provide such a safety cap or closure member for a liquid radioactive iodine solution container that is very inexpensive to produce so that, after its use by the patient, both the container and safety cap or closure member may be discarded.

Toward these and other ends, the present invention provides a cap or closure member that replaces the conventional cap or closure member provided with the conventional container for storing therein liquid radioactive iodine solution. The safety cap of the present invention includes a pair of through-holes formed in the upper portion of the cap, which extend downwardly through the cap so as to receive a pair of plastic, flexible straws, or the like. Each of the straws extends through the upper portion of the cap such that the lower end of each straw is exposed to the interior of the container containing the liquid radioactive iodine solution. The interior of the cap of the present invention is provided with a sealing member that allows for a force-fit of each of the straws in the through-holes which may, thus, allow for the firm sealing of the straws in the holes and the fixation of the portions of the straws in the holes of the cap, so that the portions of the straws extending through the holes in the cap may not be moved relative to the cap, which provides a firm vacuum seal thereof.

In using the safety cap of the present invention, one merely removes the standard cap from the conventional container storing the liquid radioactive iodine solution, and replaces it with the safety cap of the present invention. Thereafter, the portion of the one straw that extends out of the interior of the container is used by the patient for drinking the liquid radioactive iodine solution in the container. After the contents of the container have been drunk by the patient via the one straw, the end of the other straw, outside the container, is placed inside a container containing water, such as a glass. The patient then continues to draw on the exterior end of the one straw until enough of a vacuum is created to thereby draw water from the water glass into the interior of the container holding a residue of the radioactive iodine solution, thereby flushing the interior of the container. Continued drawing on the one straw will allow the patient to drink the water and remaining liquid radioactive iodine solution mixture in the interior of the container. For each of the several flushings of the interior of the container, the patient will suck or draw on the straw until enough water is sucked into the interior of the container such that the level of the water reaches the interior end of the one straw upon which the patient is drawing. At that time, the end of the other straw in the water container will be removed and the patient will drink the entire mixture of water and remaining liquid radioactive iodine solution in the container by tilting the container, upon completion of which the process is repeated for several fillings of the container.

BRIEF DESCRIPTION OF THE DRAWING

The invention will be more readily understood with reference to the accompanying drawing, wherein:

FIG. 1 is a perspective view showing the safety cap for containers of liquid radioactive iodine solution of the present invention;

FIG. 2 is a perspective view showing the cap of FIG. 1 in place on a conventional container storing liquid radioactive iodine solution, in combination with a water glass in which is placed one end of one of the straws of the safety cap of the present invention;

FIG. 3 is a cross-sectional view taken along line 3—3 of FIG. 2; and

FIG. 4 is a cross-sectional view taken along line 4—4 of FIG. 2.

DETAILED DESCRIPTION OF THE INVENTION

Referring now to the drawing in greater detail, the safety cap for attachment to a conventional container for liquid radioactive iodine solution is shown in FIG. 1, and is indicated generally by reference numeral 10. The safety cap 10 includes a main portion 12 formed as a typical cap having interior female threads for screwing onto the top neck-portion of the container. The female threads are indicated generally by reference number 14 in FIG. 4, and cooperate with male threads 16 of the neck of the bottle 20, so that a tight fit of the cap on the bottle may be achieved, in a conventional manner. The main portion 12 includes an upper section 22 through which are provided a pair of through-holes 30 and 32. A pair of clear, plastic straws 40 and 42 are also provided or formed for insertion through the through-holes 30 and 32, respectively, as can be seen clearly in FIG. 1. The straw 42 includes a lower end 42' that is received in the interior of the bottle 20, when the cap 10 is mounted thereto, and a second end 42'' which lies exteriorly of the interior of the bottle, when the cap is mounted to the bottle, which end 42'' is used by the patient for drawing out the contents of the bottle 20. The straw 40 includes a lower end 40' that also extends into the interior of the bottle 20, when the cap 10 is mounted thereto, and an end 40'' exterior of the interior of the bottle 20, when the cap 10 is mounted thereto, which end 40'' is insertable into the interior of a glass containing water therein, as shown clearly in FIG. 2. The glass of water 50 is used in the method of administering the liquid radioactive iodine solution in the bottle 20 in a manner to be described hereinbelow. As can be seen in FIG. 2, the end 42' of the straw 42 extends downwardly into the interior of the bottle 20, such that it reaches almost to the bottom 20' thereof. This is to ensure that most of the contents of the bottle 20, which contents comprise the solution of liquid radioactive iodine, may be drunk via the straw 42. Of course, in the usual manner, the contents of the bottle 20 may be drunk to the best of one's ability by tilting the bottle 20 at a desired angle so that the liquid in the bottle attains to the level of the end 42' therein. The end 40' of the straw 40 need not extend far into the interior of the bottle; all that is required of the end 40' is that it be exposed to the interior of the bottle 20, so that it may draw water in the glass 50 into the interior of the bottle after a partial vacuum has been formed in the interior of the bottle by removing air therein via the straw 42.

It is, of course, important that the portions of the straws 40 and 42 extending through the upper section 22 of the cap 10 be sealed, so that at least a partial vacuum may be formed in the interior of the bottle 20. It is possible to provide such a seal by simply force-fitting portions of the straws 40 and 42 through holes 30 and 32, so that a tight fit exists, to thereby prevent any exposure of the interior of the bottle 20 to the ambient air.

Since the contents of the bottle 20 are radioactive, it is important to provide as many safety features as possible. Toward this end, the cap 10 is provided with an inner mounting and sealing member, indicated generally by reference number 58, as shown in FIG. 4. This mounting and sealing member 58 is preferably made of a hard plastic, such as polyurethane, and may be generally frustro-conical in shape, although any other shape may be used as long as mounting and sealing thereby is achieved. As can be seen in FIG. 4, each of the holes 30 and 32 extends generally through the portions of the mounting and sealing member 58 directly juxtaposed thereto, so that portions of the straws 40 and 42 may extend through the mounting and sealing member 58, so that the ends 40' and 42' may communicate with the interior of the bottle 20. The mounting and sealing member 58 is preferably provided with a strong adhesive bonding material that firmly adheres the outer area of the respective straw portions of straws 40 and 42 to the mounting and sealing member 58, so that the straws 40 and 42 are firmly fixed in place, and may not be dislodged, to prevent any accidental removal of the straws 40 and 42 and any resulting possible exposure of radioactivity to any person and to the ambient air.

It is also within the purview and scope of the present invention to provide a simple force-fit for the portions of the straws 40 and 42 extending through the mounting and sealing member 58, the length of the passage of the holes formed in the mounting and sealing member 58 providing a sufficient length and frictional force to prevent any accidental slippage of the portions of the straws 40 and 42, to thereby provide an adequate seal for the purposes intended. Of course, a tight, bonded fixation of the portions of the straws in the mounting and sealing member is preferential, so as to prevent any accidental removal of the straws from the interior of the bottle.

The cap 10 may be made of any hard, plastic material such as polyurethane, polypropylene, polyethylene, and the like. It is also possible to form the mounting and sealing member 58 from any hard plastic, while making the straws 40 and 42 from a somewhat flexible thermoplastic polyolefin. In the embodiment where only force-fitting is used, without the adhesive bonding, the straws 40 and 42 should be provided in a diametric extension such that the flexibility thereof allows for the insertion of portions of the straws through the through-holes 30 and 32, and the passages directly beneath through-holes 30 and 32 in the mounting and sealing member 58, such that the straws in these portions may be subsequently compressed to form a tight force-fit therein. It is, of course, also possible to form portions of straws 40 and 42, extending through the cap 10, and the cap 10 itself as one, integral, pre-molded material, thereby providing an even greater bond; thereafter, the remaining length of straws 40 and 42 may be secured by any conventional attaching means to form the elongated straws indicated in FIGS. 1 and 2. In the case of the pre-molded, integral cap with straw portions, it is possible to entirely do away with the mounting and sealing member 58. For larger-sized bottles, however, it may be useful to include such mounting and sealing member 58 to provide added structural integrity and additional prevention of accidental removal of any straw portion in the cap.

According to the method of using the safety cap 10 of the present invention, the standard cap provided with the conventional bottle 20 is removed by a technician suitably protected from radioactivity. After removal of the conventional cap of the bottle 20, the cap 10 of the present invention is screwed on the bottle to replace the removed conventional cap. The cap 10 is considerably tightened on the upper neck portion of the bottle 20, so that a tight seal is formed, in order to allow for creation of a partial vacuum within the interior of the bottle. Thereafter, the end 42″ of the straw 42 is inserted into the patient's mouth, and the patient draws thereon to imbibe the liquid radioactive iodine solution contained in the bottle 20. When most of the liquid radioactive iodine solution is drunk by the patient, with very little remaining under the end 42′, the end 40″ of the straw 40 is inserted into the glass of water 50 such that the end 40″ is immersed in the water. At this juncture, the straw 42″ is reinserted into the patient's mouth and the patient draws thereon to provide a partial vacuum in the interior of the bottle 20, thereby causing the drawing of water in glass 50 into the interior of the bottle 20. When enough of the water from glass 50 is drawn into the bottle 20, in order to reach the level defined by the end 42′, the end of the straw 40″ is removed from the glass 50, and then the patient tilts the bottle and sucks on the straw to drink the mixture of water and residue of the liquid radioactive iodine solution in container 20. After the patient has finished drinking the water and liquid radioactive iodine mixture, the end 40″ is reinserted into the glass of water 50, and the process is repeated, several times. Typically, this refilling action with the water from the glass 50 is carried out three times. Thus, it can be seen, that the entire process of drinking the liquid radioactive iodine solution in the bottle 20, and the subsequent refillings with water for mixing with the remaining portions of the liquid radioactive iodine solution, is carried out free from exposing the contents of the bottle 20 to the ambient air.

It is also noted that before placing the end of the straw 42″ into the patient's mouth, each of the ends 40″ and 42″ of the straws 40 and 42 is preferably provided with a small plastic plug (not shown) for insertion into a respective end 40″ and 42″, so that radioactivity of the liquid radioactive iodine solution in the container 20 is not diffused to the ambient air via the straws 40 and 42. These plugs for the ends 40″ and 42″ are removed just prior to the insertion of the appropriate ends into their respective sites.

An added safety feature may be achieved by sealing, by conventional heat-sealing techniques, each end of the straws 40″ and 42″ prior to filling the container with the liquid radioactive iodine solution. Such sealing of the ends of straws 40″ and 42″, in combination with the features of cap 10, may be carried out at the manufacturing level, so that, after filling the bottle 20 with the liquid radioactive iodine solution, the cap 10 may be tightly placed on the bottle 20. Upon delivery to the patient, the sealed ends of straws 40″ and 42″ may be cut with scissors, or the like. By this means, contamination of the ambient air by the contents of the bottle will be eliminated until such time as the patient is ready to drink the liquid radioactive iodine solution. The step of sealing the ends of straws 40″ and 42″ would eliminate the need for medical personnel to replace the conventional cap of bottle 20 with cap 10 of the invention, and would eliminate any contact with the radioactive material prior to the patient's use.

It is also possible to provide, at the manufacturing level, a single, elongated straw (not shown) having ends 40′ and 42′ inserted into the interior of the container 20, as shown in the drawings with the remainder of the straw positioned exteriorly of the bottle. When it is desired to administer the liquid radioactive iodine solution to the patient, the medical technicial need only cut an outer, exterior middle portion of the straw to form two straws 40 and 42, and ends 40″ and 42″. The straw should be cut in such a way so as to provide one length sufficient for immersion in water glass 50, and the other length sufficient to reach the patient's mouth.

While a specific embodiment of the invention has been shown and described, it is to be understood that numerous changes and modifications thereof may be made without departing from the scope, spirit and intent of the invention as set out in the appended claims.

What is claimed is:

1. A method of administering liquid solution contained in a bottle, or the like, which bottle is closed by a closure member through which extends a pair of straws; each of said pair of straws having an inner end in fluid communication with the interior of the container or the like, and an outer end exposed to the ambient air, wherein said method comprises:

(a) inserting the outer end of the first of the pair of straws into the patient's mouth for subsequent drawing thereon to drink the contents of the bottle, or the like;

(b) inserting the outer end of the second of the pair of straws into a container having a liquid therein, such that the outer end of the second of the pair of straws is immersed in the liquid;

(c) drawing on the outer end of the first of the pair of straws to draw liquid into the interior of the bottle, or the like, from the container having liquid therein via the outer end of the second of the pair of straws; and (d) drawing out the liquid mixture in the interior of the bottle, or the like, provided through step (c), from the interior of the bottle to the outside thereof by drawing on the outer end of the first of the pair of straws.

2. The method according to claim 1, wherein said step of drawing liquid into the interior of the bottle is carried out a plurality of times, and said step of drawing out the liquid from the interior to the outside of the bottle is carried out a plurality of times also.

3. The method according to claim 2, wherein each of said steps of drawing out the liquid from the interior of the bottle, or the like, is carried out immediately after one of said steps of drawing liquid into the interior of said bottle, or the like.

4. A dispenser for a liquid to administer the liquid to a patient, comprising:

a main container in which is stored a liquid, or the like;

a liquid, radioactive solution provided in said main container, for use in treating a patient by the imbibing of said solution;

a closure member for closing off said main container to provide a fluid-tight seal thereof, so that at least a partial vacuum may be formed in the interior of said main container;

said closure member having at least one through-opening passing entirely therethrough;

straw means having a first section and a second section, said first and second sections being received and passing through said at least one through-opening of said closure member;

means for fixedly and permanently positioning and sealing a part of each of said first and second sections in said at least one through-opening so that each said part of said sections is fixed permanently in place and sealed and may not be removed from said through-opening, in order to ensure that no radioactivity escapes through said closure member via through said at least one through-opening;

said first section having a first, open end positioned in the interior of said main container and extending into said interior a certain distance; and said second section having a second, open end also positioned in said interior of said main container, said second, open end extending into said interior a greater distance than said first, open end;

each of said first and second sections also having a portion thereof positioned exteriorly of said interior and said at least one through-opening of sufficient length to allow access thereto by a patient, so that the patient may draw on said second section and drink said radioactive liquid solution in said main container in a safe manner, and to allow for insertion of said portion of said first section of said straw means into a container of water, or the like.

5. The dispenser according to claim 4, wherein said closure member comprises a screw-on cap having an undersurface thereof facing the interior of said main container when said closure member is mounted thereto, said cap matingly engaging with the upper portion of said main container; said means for permanently and fixedly positioning and sealing comprising an insert member mounted to said cap on said undersurface thereof.

6. The dispenser according to claim 5, wherein each of said cap and said insert member comprises a pair of through-holes, said pair of through-holes of said insert member constituting said at least one through-opening of said closure member, each of said pair of through-holes of said insert being in colinear alignment with a respective one of said pair of through-holes of said cap, so that said first and second sections of said straw means may be positioned respectively therein; said means for fixedly and permanently positioning and sealing further comprising bonding means for respectively fixedly bonding said parts of said first and second sections in said pair of through-holes of said insert member.

7. The dispenser according to claim 6, wherein said insert member is substantially frustro-conical in shape, and said first section of said straw means comprises a third, exterior open end, and said second section of said straw means comprises a fourth, exterior open end, said third, open end being insertable into a container of water, and said fourth, open end being insertable into the mouth of a patient.

* * * * *